(12) United States Patent
Colombi

(10) Patent No.: US 11,033,730 B2
(45) Date of Patent: Jun. 15, 2021

(54) APPARATUS FOR THERAPEUTIC TREATMENT OF TISSUE INJURIES

(71) Applicant: MCC SISTEMI s.r.l., Cassina de' Peseta (IT)

(72) Inventor: Maurizio Colombi, Milan (IT)

(73) Assignee: MCC SISTEMI S.R.L., Cassina de' Pecchi (IT)

( * ) Notice: Subject to any disclaimer, the term of this patent is extended or adjusted under 35 U.S.C. 154(b) by 237 days.

(21) Appl. No.: 16/322,540

(22) PCT Filed: Jul. 25, 2017

(86) PCT No.: PCT/IB2017/054493
§ 371 (c)(1),
(2) Date: Feb. 1, 2019

(87) PCT Pub. No.: WO2018/025118
PCT Pub. Date: Feb. 8, 2018

(65) Prior Publication Data
US 2019/0184154 A1    Jun. 20, 2019

(30) Foreign Application Priority Data
Aug. 1, 2016    (IT) .............................. 1020160080827

(51) Int. Cl.
*A61N 1/04*    (2006.01)
*A61N 1/36*    (2006.01)
(Continued)

(52) U.S. Cl.
CPC .......... *A61N 1/0468* (2013.01); *A61M 35/00* (2013.01); *A61N 1/0476* (2013.01); *A61N 1/32* (2013.01);
(Continued)

(58) Field of Classification Search
CPC .......... A61N 1/0468; A61N 1/44; A61N 1/32; A61N 1/0476; A61N 1/36014; A61M 35/00; A61M 2202/0216; A61M 2205/054
See application file for complete search history.

(56) References Cited

U.S. PATENT DOCUMENTS

| 5,975,090 A | 11/1999 | Taylor et al. |
| 2003/0050674 A1 | 3/2003 | Joshi |

(Continued)

FOREIGN PATENT DOCUMENTS

| DE | 10 2013 113 905 A1 | 6/2015 |
| KR | 2013-0023588 A | 3/2013 |

(Continued)

OTHER PUBLICATIONS

International Search Report, dated Nov. 20, 2017.
(Continued)

*Primary Examiner* — Bradley J Osinski
(74) *Attorney, Agent, or Firm* — Jacobson Holman PLLC

(57) ABSTRACT

An apparatus (1) far the therapeutic treatment of a user's tissue injury comprising a control unit (2), to which aft applicator (3) is connected adapted to be positioned in proximity of the tissue injury to be treated is described, said control unit (2) being configured to generate at the applicator (3) an electric field adapted to be applied on the tissue injury. The control unit (2) is also configured, to generate an air or oxygen flow which is directed to the applicator (3), and to transform at the applicator (3) the air or oxygen flow into an ozone flow adapted to be diffused and applied on the tissue injury in combination with said electric field.

14 Claims, 8 Drawing Sheets

(51) Int. Cl.
  *A61N 1/44* (2006.01)
  *A61N 1/32* (2006.01)
  *A61M 35/00* (2006.01)
  *A61M 37/00* (2006.01)

(52) U.S. Cl.
  CPC ........... *A61N 1/36014* (2013.01); *A61N 1/44* (2013.01); *A61M 2037/0007* (2013.01); *A61M 2202/0216* (2013.01); *A61M 2205/054* (2013.01)

(56) References Cited

U.S. PATENT DOCUMENTS

| | | | |
|---|---|---|---|
| 2007/0055337 A1* | 3/2007 | Tanrisever | A61N 1/44 607/154 |
| 2014/0200506 A1 | 7/2014 | Zemel et al. | |
| 2015/0216816 A1 | 8/2015 | O'Neil et al. | |
| 2015/0327963 A1 | 11/2015 | Fregoso et al. | |
| 2016/0023183 A1 | 1/2016 | Levin | |
| 2016/0287892 A1* | 10/2016 | Nettesheim | A61F 13/00059 |
| 2019/0105506 A1* | 4/2019 | Bourquin | A61N 1/44 |

FOREIGN PATENT DOCUMENTS

| | | |
|---|---|---|
| WO | 2013/040542 A1 | 3/2013 |
| WO | 2014/143412 A1 | 9/2014 |
| WO | 2015/028822 A1 | 3/2015 |

OTHER PUBLICATIONS

L. Fletcher et al., "Bactericidal action of positive and negative ions in air", BMC Microbiology, vol. 7, No. 1, Apr. 17, 2007, pp. 1-9, cited in the ISR.

R. Unal, "Inactivation of *Escherichia coli* O157:H7, Listeria monocytogenes, and *Lactobacillus leichmannii* by Combinations of Ozone and Pulsed Electric Field", Journal of Food Protection, vol. 64, No. 6, Jun. 2001, pp. 777-782, cited in the ISR.

* cited by examiner

APPARATUS FOR THERAPEUTIC TREATMENT OF TISSUE INJURIES

BACKGROUND OF THE INVENTION

The present invention relates to an apparatus and a method for the therapeutic treatment of tissue injuries.

Skin injuries, variably deep, are areas of tissue breakage and loss with exposure of the underlying tissues. The term "external injury" or "wound" indicates the morphological and functional destruction of the continuity of the superficial skin layers and, in the most severe cases, of the deep subcutaneous ones.

The injuries are evaluated and catalogued according to their amplitude, depth and characteristics. The mild superficial injuries affect only the epidermis, the dermis, and at most a part of the hypoderm; the deepest and most severe ones involve all the subcutaneous tissue (adipose tissue) up to the muscles, the periosteum, causing the exposure of bone or support structures (tendons and cartilages); the most severe (chronic) ones are characterized by loss of substance at skin level and poor healing tendency.

Typical tissue injuries are, for example, pressure injuries (or decubitus ulcers), which are commonly referred to as "sores". The sores are the direct consequence of a high or prolonged compression, or of cutting forces (or stretching), causing a mechanical stress to the tissues and shrinkage of blood vessels.

A pressure injury histologically always tends to become chronic rather than to spontaneously heal. For this reason, there are treatments with techniques capable of reactivating tissue repair processes by inhibiting chronicity processes.

One of the most modern therapeutic treatment methods is the regenotherapy which, to accelerate tissue reconstruction, uses a radio frequency signal between 1 MHz and 400 MHz transmitted by suitable antennas with limited signal strength (0.15 mW) to affect tissues. The effect is to improve the cellular respiration, and to accelerate the cellular exchange, resulting in the reconstruction of the tissue affected by the injury.

The signal produced by the instrument through which regenotherapy is performed, causes a modification, of the permeability of the cytoplasmic membrane with resulting electrolytic re-balancing. Where a pathological failure exists, the application of these defined radio frequency signals causes an internal and external re-balancing to the cell.

The application of high modulated and pulsed frequencies gives all the benefits of radio waves penetration, without appreciably warming the tissues, due to the relatively long pauses between impulses.

The regenotherapy exerts good effects on connective tissue and venous and arterial diseases of all kinds, wherein it was determined that controlled electromagnetic fields force the synthesis of hyaluronic acid, a basic constituent of connective substance and pericapillary sleeve.

However, treatment times are often long, since the expected number of applications is between 10 and 20, or sometimes even higher, depending on the severity of each ease and the competent, physician's discretion, each application lasting about 30 minutes.

BRIEF SUMMARY OF THE INVENTION

The object of the present invention is to provide an innovative apparatus for enhancing the effects of current therapeutic treatment techniques for tissue injuries.

Another object of the present invention is to provide a method for speeding up tissue regeneration processes.

According to the invention, this object is achieved with an apparatus for the therapeutic treatment of a tissue injury.

DESCRIPTION OF THE DRAWINGS

These and other features of the present invention will be made more apparent from the following detailed description in a practical embodiment thereof illustrated by way of not limiting example in the appended drawings, wherein.

DETAILED DESCRIPTION OF THE INVENTION

Figure 1:
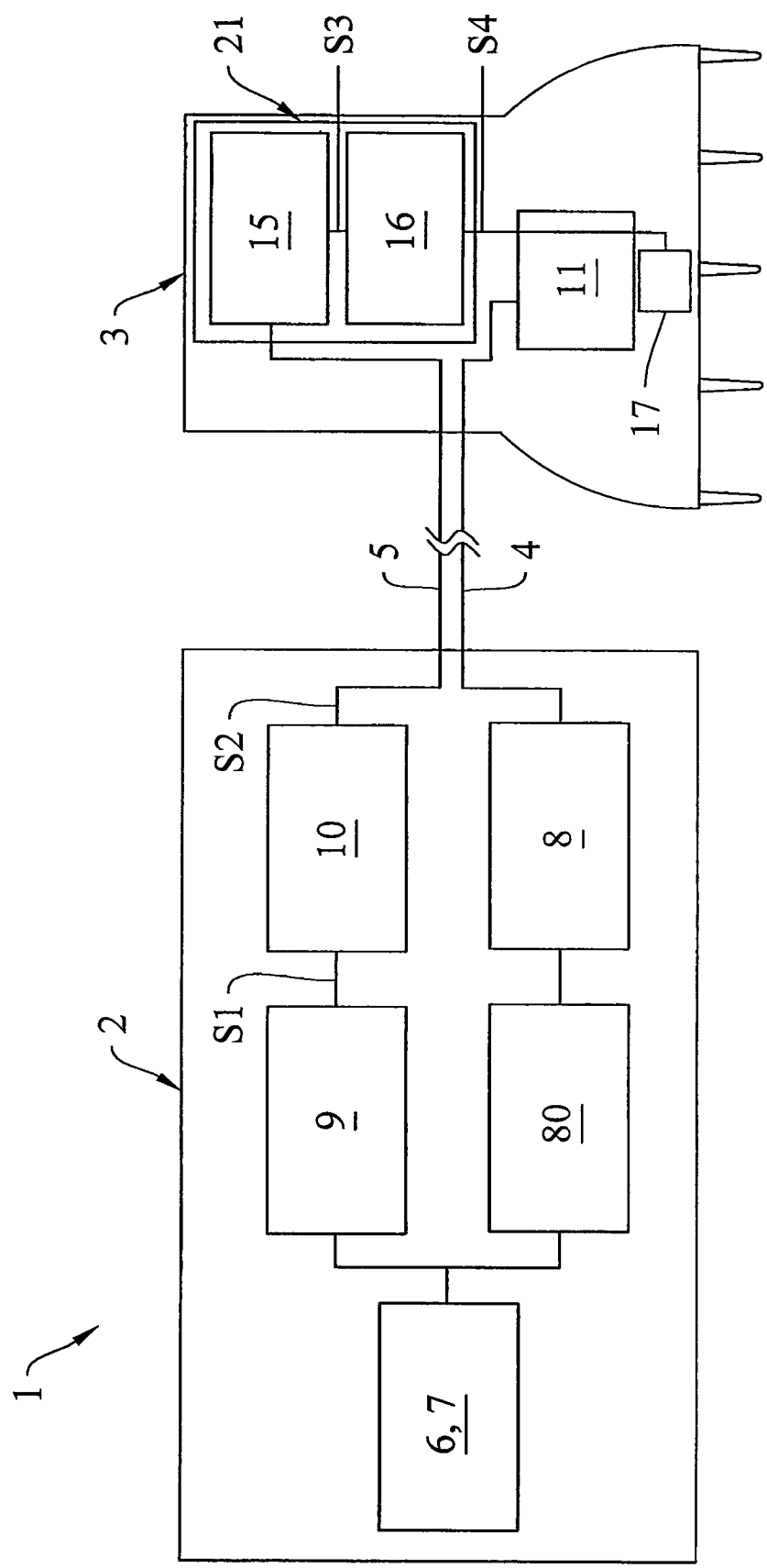
FIG. 1 shows a schematic view of an apparatus for the therapeutic treatment of a tissue injury according to a first embodiment of the present invention.

FIG. 1 schematically, shows an apparatus 1, according to the present invention, for the therapeutic treatment of a tissue injury.

The apparatus 1 substantially comprises a control unit 2 through which to operate the apparatus 1 by adjusting at least one parameter, and an applicator 3 adapted to be positioned m proximity of the tissue injury to be treated, said applicator 3 being in fluid and M electric connection with the control unit 2.

The connection of applicator 3 to the control unit 2 is configured by means of a connecting tube 4 for air or oxygen passage and at least art electric cable 5 for the electric connection.

The control unit 2 is configured to generate, at applicator 3, an electric field to be applied to the tissue injury and to generate also an air or oxygen flow which is converted into ozone still at said applicator 3 to be diffused and applied to the tissue injury along with said electric field, synergistically enhancing the therapeutic effect.

In particular, the control unit 2 comprises an electric power supply 6 adapted to convert the maim voltage (with alternating waveform, maximum value 220 V and frequency 50 Hz) to a continuous supply voltage, such as at 12-13 V. Alternatively, the power can be supplied directly from a lithium polymer rechargeable battery 7.

The electric power supply 6, or the batteries 7, provide electric power to at least one electric pump 8 adapted to generate an air or oxygen flow which, through the connecting tube 4, is sent to applicator 3. The electric pump 8 is provided with a first regulator 80 by means of which it is possible to start, modify its flow rate, or stop the air or oxygen flow conveyed to applicator 3.

In addition, the control unit 2 comprises an oscillator 9 for generating a first electric signal S1 with a rectangular waveform having a frequency of between 500-5000 Hz, a maximum current value of about 50 mA and a maximum voltage value of between 12-13 V.

The first electric signal S1 is amplified by a power stage 10 (e.g., a FET) placed downstream of oscillator 9. A second electric signal S2 will therefore be provided at the output to the power stage 10, again with a rectangular waveform at the same frequency as the first electric signal S1 with a current value of about 3 A and a maximum voltage value of approximately 100 V.

Figure 2:
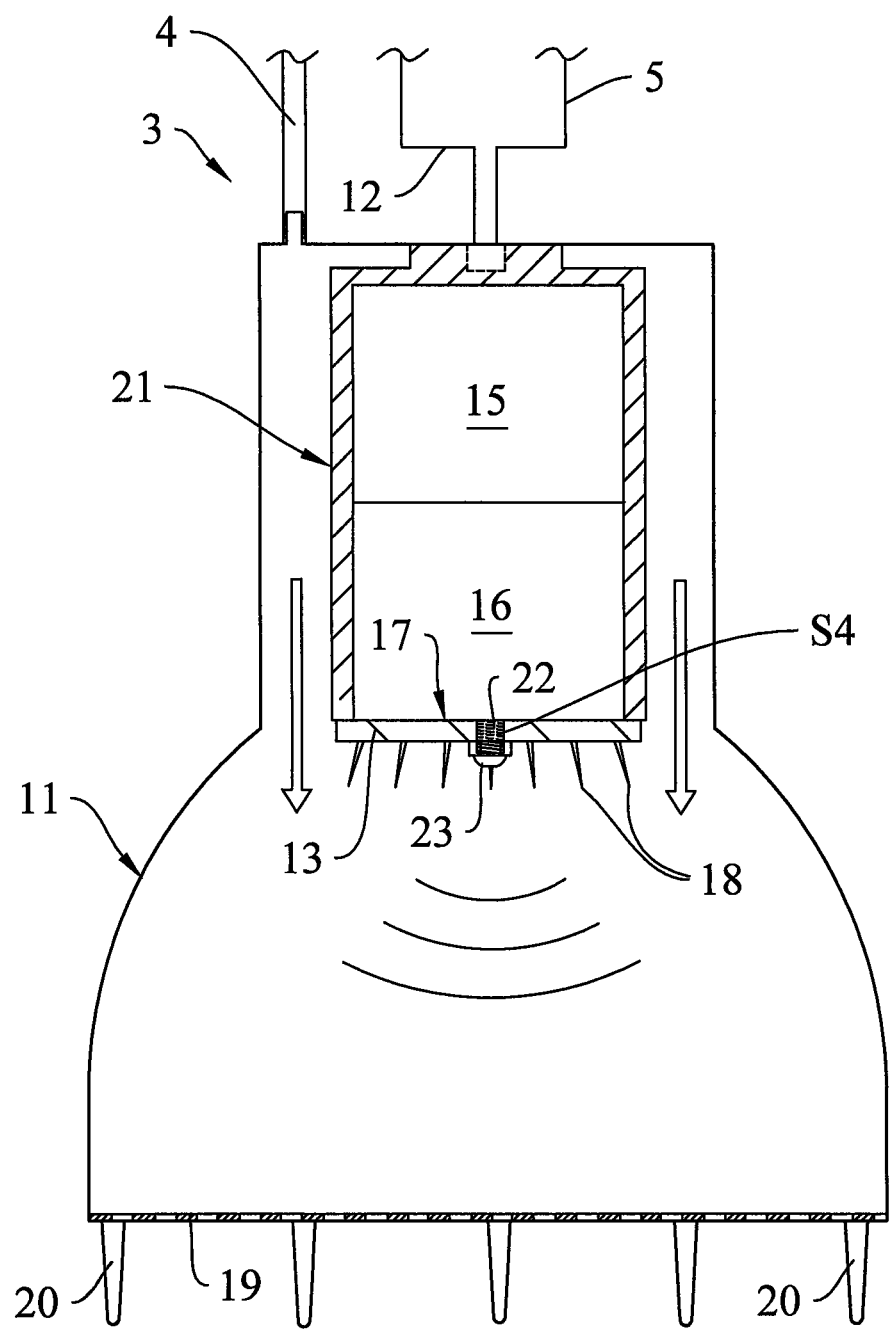
FIG. 2 shows a partial section view of an applicator comprised in the apparatus of FIG. 1.

On the other hand, applicator 3 (FIG. 2) provides for a diffuser 11 in which the air or oxygen from the pump 8 is conveyed, through the connection tube 4. The diffuser 11 comprises a bottom grid 19 (FIG. 4) of a non-conductive material adapted to diffuse air or oxygen, so that these gases may affect a larger area.

Within applicator 3 there is also a high voltage generator 21 (FIGS. 1, 2) housed and embedded in a high-dielectric rigidity plastic cylinder.

The high voltage generator 21 comprises a transformer 15 connected to the power stage 10 by means of the electric cable 5 and having in input the second electric signal S2. The transformer 15 has the function of modifying the voltage and the current of the second electric signal S2, by providing a third electric signal S3 in output with a sawtooth waveform, with a maximum voltage value of about 10 KV, with a value of current of about 0.5 mA and which maintains the frequency value of the second electric signal S2.

To increase the voltage value of the third electric signal S3, downstream of the transformer 15, the high voltage generator 21 comprises a voltage multiplier 16 (FIGS. 1, 2) comprising a plurality of diode-capacitor multiplier cells. For example, the voltage multiplier 16 comprises 6 multiplier cells.

The voltage multiplier 16 is adapted to receive said third electric signal S3 and to provide a fourth electric output signal S4 which is rectified and is equal to the maximum value of the third electric signal S3 multiplied by the number of diode-capacitor multiplier cells present in the voltage multiplier 16 (in this ease multiplied by 6). Typically, the voltage value of the fourth electric signal S4, which, as said, is a continuous signal, is about 6-60 KY.

The fourth electric signal S4 is supplied to an electrode 17 by means of a screw stem 22 placed below and in electric connection with the high voltage generator 21, said electrode 17 being also present within applicator 3 and adapted to generate said electric field to be applied to the tissue injury.

Figure 3:
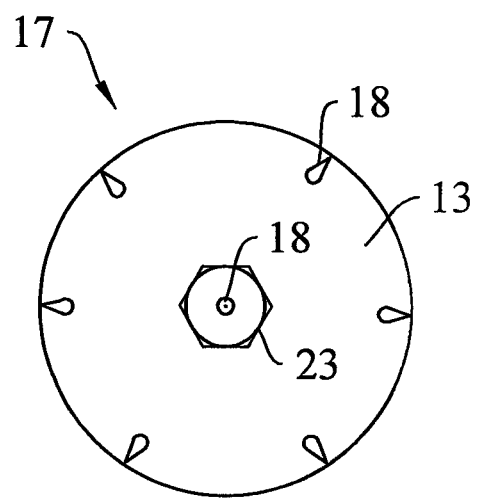
FIG. 3 shows a front view of an electrode included in the applicator of FIG. 2.

The electrode 17 is placed internally to the diffuser 11 (FIG. 2) and comprises a conductive plate 13 with a central hole, through which the screw stem 22 is inserted in contact, and also includes a plurality of sharp conductive elements 18 extending from the same conductive plate 13 (FIG. 3). Preferably, the sharp conductive elements 18 are arranged along a circumference on a lower side of the conductive plate 13, they are mutually equidistant and also substantially radially directed, i.e., each sharp conductor 18 has a given inclination relative to the perpendicular to the plane of fee conductive plate 13.

For fixing the electrode 17 to the high voltage generator 21, a locking nut 23 (self-locking or blind) adapted to screw on said screw stem 22 is present, and centrally having itself a further sharp conductive element 18.

The grid 19 is placed in front of the sharp conductive elements 18 at a safe ty distance of about 55-60 mm m such a way as to avoid the direct contact of the sharp conductive elements 18 with the patient, but especially to apply a suitable value electric field to the tissue injury, considering that the dielectric strength of the humid air is about 1 KV/mm.

Figure 4:
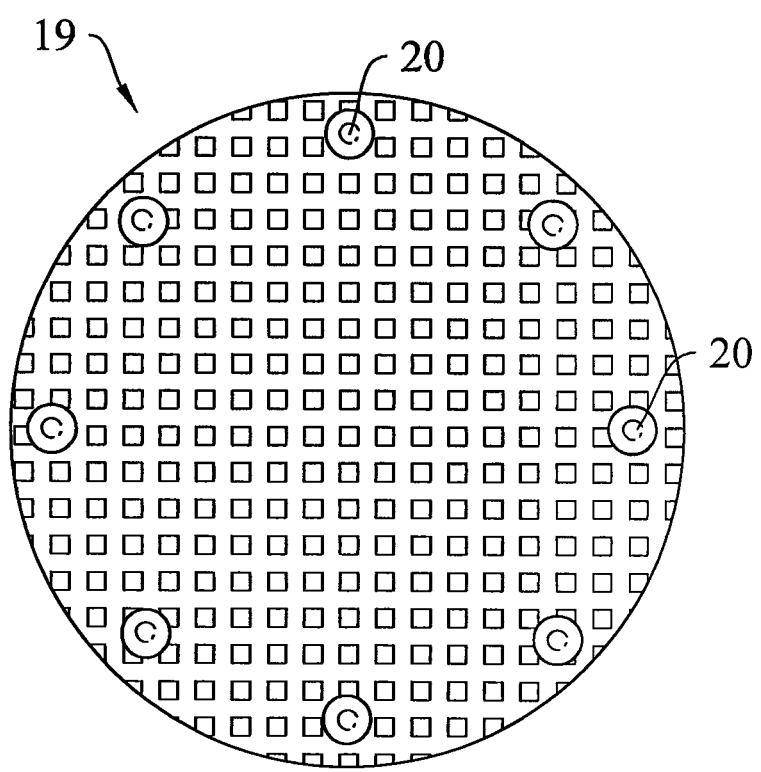
FIG. 4 shows a front view of a grid included in the applicator of FIG. 2.
Figure 5:
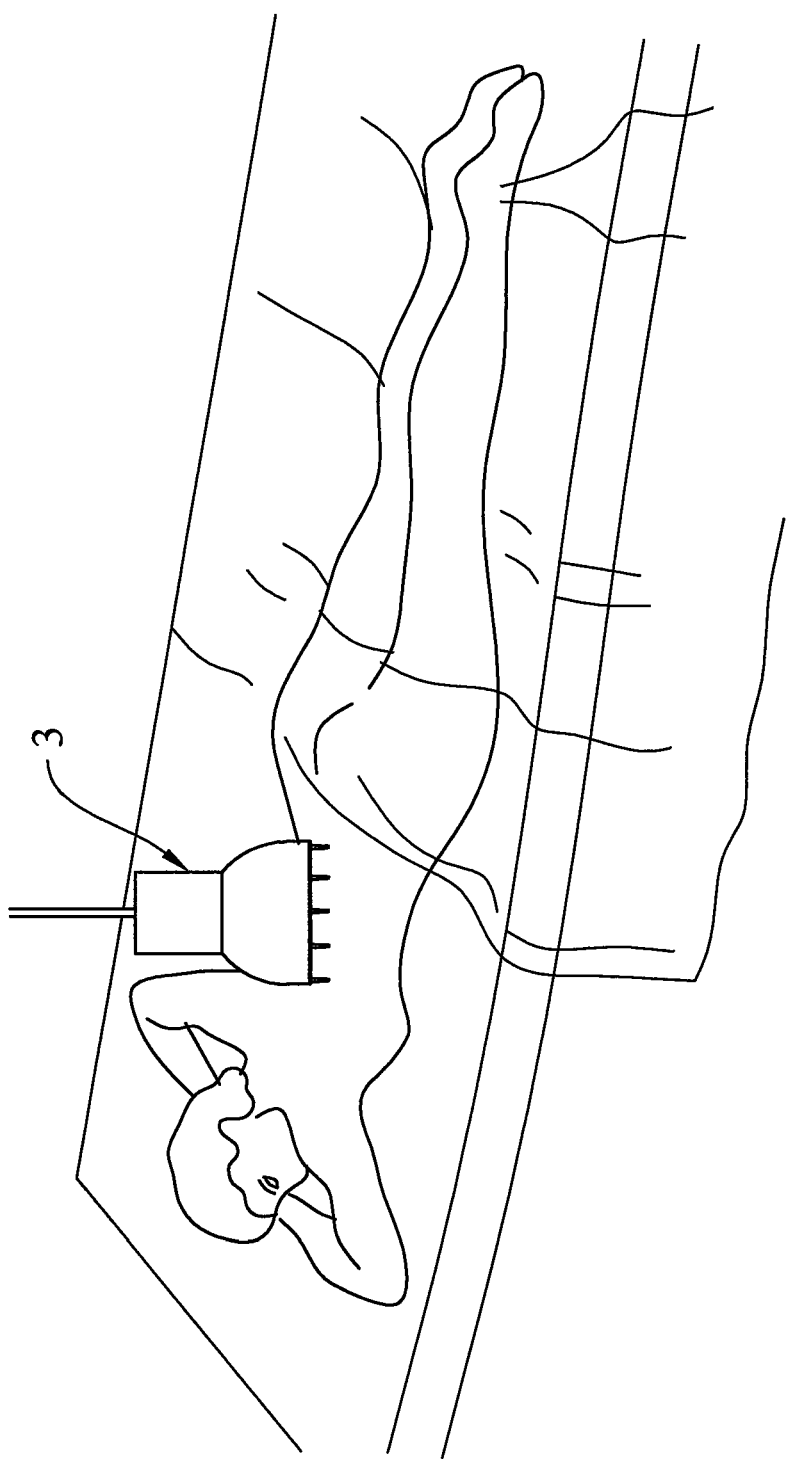
FIG. 5 shows an example of use of the apparatus of FIG. 1.

Advantageously, a plurality of pins 20 of about 5 mm in length may be present on the surface 13 of the grid 19 (FIG. 2), said pins 20 being adapted to contact the patient's skin in proximity of the tissue injury, avoiding the direct contact of the grid 19 with the tissue injury. As shown in FIG. 4, the pins 20 are arranged along a circumference in the outer portion of the grid 19, so that they can contact the skin on healthy areas, externally surrounding the tissue injury to be treated. For example, the grid 19 includes 8 pins 20.

It has been said that the electrode 17 is at a high electric potential (6-60 KV). In this high potential condition, the charge density tends to be higher in the sharp portion of each conductive element 18 (for the phenomenon known as "dispersing power of the tips"), producing an electric Held at the tips that is greater than in the rest of the electrode 17. By means of a second regulator, it is possible to modify the electric field by varying the electric potential of the electrode 17.

In addition, the high electric field of the tips causes ionization of the air or oxygen flow which is conveyed within the diffuser 11, triggering a plurality of electric discharges (the so-called "crown effect") starting from the sharp part of each, of the conductive elements 18. The modification of the electric potential applied to the electrode 17 results in an increase or a decrease in the electric discharges generated by the crown effect; specifically, the electric discharges increase as the electric potential increases on the electrode 17.

Preferably, a return electrode (not shown in FIGS. 1-5), electrically connected through an electric cable 12 to a reference potential V1, for example 100 milliVolt, and applied to the patient via, e.g., a patch in a position near to the tissue injury, and the arrangement of applicator 3 on the tissue injury allows to convey the electric discharges generated by the conductive elements 18 on the tissue injury.

The passage of air or oxygen conveyed within the diffuser 11 by the electric discharges causes the production of ozone, according to the chemical reaction $3O_2 \rightarrow 2O_3$. Therefore, the modification of the electric potential applied to the electrode 17 also has the effect of increasing or decreasing the ozone concentration (the emitted ozone concentration becomes greater as the electric potential increases over the electrode 17), concentration which can also be modified by adjusting the air or oxygen flow generated by the electric pump 8.

In an alternative embodiment, applicator 3 may comprise an ultraviolet (UV) lamp instead of the circuit structure constituted by the high voltage generator 21 and electrode 17. The above chemical reaction for ozone production from air or oxygen, in this case is carried out at the passage of the oxygen in front of the UV lamp (185 nm), each molecule of oxygen disintegrating and then recombining into three atoms, generating ozone.

As said, the apparatus 1 is used to treat tissue injuries, such as pressure injuries, which, are commonly referred to as "sores". Unlike the known apparatuses, said apparatus 1 is more effective, since its operation synergically combines the effects of both the electric field and the ozone, both affecting the tissue injury. This results in an enhancement of the therapeutic effect due to the combined action of the electric field and ozone.

In particular, the electric field has the effect of improving the cellular respiration and accelerating the cellular exchange, resulting in the reconstruction of the tissue affected by the injury. The ozone, on the other hand, has the effect of improving the blood ability to bring oxygen to the tissues, resulting in the reactivation of microcirculation and peripheral oxygenation, stimulation of the reactivation of the enzymatic antioxidant defense systems of the organism, and it is a powerful agent against bacteria, fungi, viruses and parasites.

The apparatus 1 is adjustable by means of a timer for the automatic shutdown of the control unit 2 at the end of a set time.

In addition, the apparatus 1 may include a support (not shown in the Figures) comprising a base, an adjustable eight vertical rod extending from said base and an adjustable arm rotatably pivoted to said rod. At the free end of the adjustable arm there is a junction to which applicator 3 is connected, said support being studied in such a way as to allow the user to reach any area of the patient's body to be treated therapeutically.

In the operation, when apparatus 1 is used for the therapeutic treatment of a tissue injury, applicator 3 is positioned in proximity of the area to be treated i.e. on the tissue injury. The optimum distance of applicator 3 is determined by the distance of the grid 19 from the electrode 17 and from the pins 20 which, by contacting the patient's skin in the areas adjacent to the injury, on one hand, do not cause the patient suffering, and on the other hand, maximize the effectiveness of treatment on the injury, (FIG. 5); the applicator is therefore contacted with the patient's skin.

When operated, the electric pump 8 generates an air or oxygen flow that may be controlled by said first regulator 80, to increase or decrease the ozone concentration which is intended to be produced. The air or oxygen flow generated by the electric pump 8 flows through the connecting tube 4 and is collected and conveyed within the diffuser 11.

At the same time, the apparatus 1 generates at the sharp conductive elements 18 a high electric field which is adjustable through said second regulator, modifying the electric potential applied over the electrode 17.

The return electrode is advantageously positioned in contact with the patient, so that the electric field primarily affects the area of the tissue injury and then discharges over the return electrode. The effect of the electric field is to improve the cellular respiration and accelerate the cellular exchange, resulting in the reconstruction of the injured tissue.

The electric field also causes the ionisation of the air or oxygen flow conveyed within the diffuse 11, triggering electric discharges that, starting from the sharp conductive elements 18 of the electrode 17, discharge in the direction of the return electrode. Such electric discharges transform the air or oxygen flow conveyed within the diffuser 11 into an ozone flow, with a concentration determined also by the regulation through the second potential regulator on the electrode 17. The ozone flow is diffused and directed to the tissue injury and, as said, has the effect of improving the blood ability to bring oxygen to tissues, stimulate the reactivation of the enzymatic antioxidant defense systems of the organism, and is a very potent agent against bacteria, fungi, viruses and parasites.

Preferably, the treatment provides for daily sessions, each of 15-30 minutes, depending on the ease.

The contraindications are the usual ones for devices using electric fields: therefore, they should not be used hi the ease of patients with cardiac pacemakers, pregnant women, patients with metal prostheses in proximity of the area to be treated.

Due to the combination of electric field and ozone generated by the apparatus, according to the present invention, there is therefore a synergistic enhancement of the therapeutic effect on the tissue injury, with a healing time of the tissue injuries that can be considerably reduced with respect to the known treatment techniques.

FIGS. 6-9 illustrate an apparatus for the therapeutic treatment of a tissue injury according to a second embodiment of the present invention.

The apparatus of FIGS. 6-9 differs from the apparatus of FIGS. 1-5 only for the different type of applicator 30 used and since the control unit 2 is adapted to convey within applicator 30 only an air flow and not an oxygen flow. Said applicator 30 is in fluid and in electric connection with the control unit 2. The connection of applicator 30 to the control unit 2 is carried out by means of the connecting tube 4 for the passage of air and the electric cable 5 for the electric connection.

Figure 7:
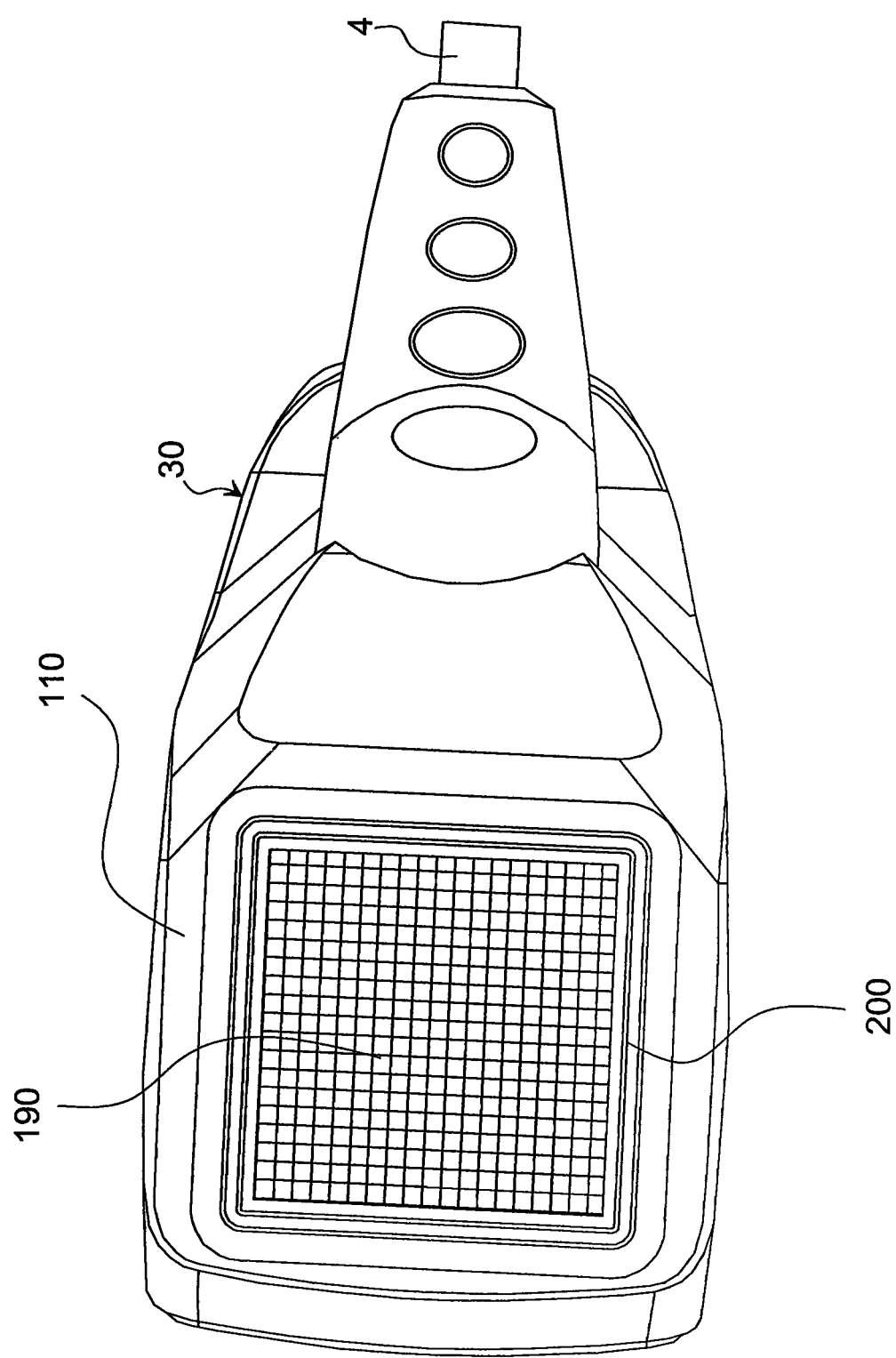
FIG. 7 shows a perspective view of the applicator of the apparatus of FIG. 6.
Figure 8:
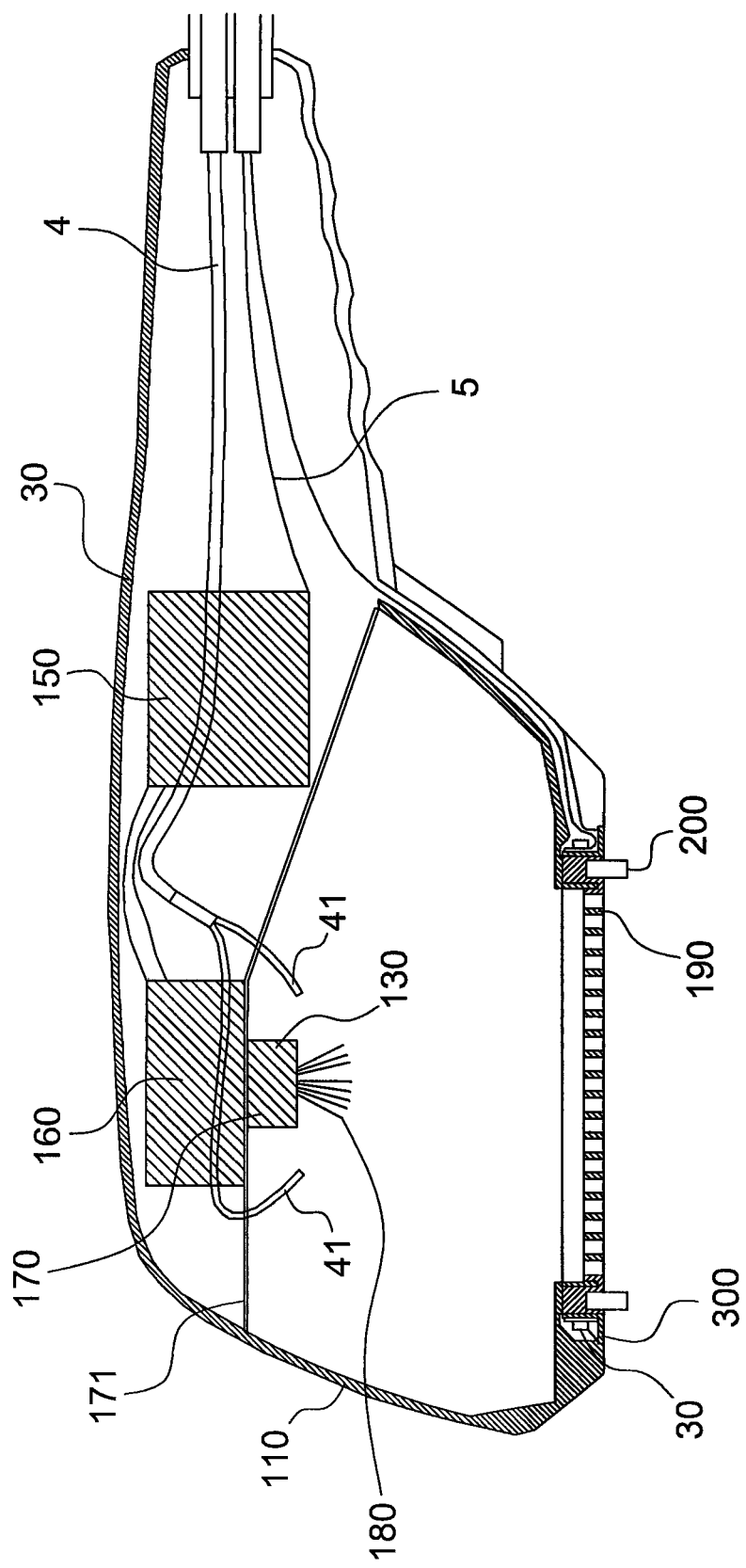
FIG. 8 is a cross-sectional view of the applicator of FIG. 6 in rest position.
Figure 9:
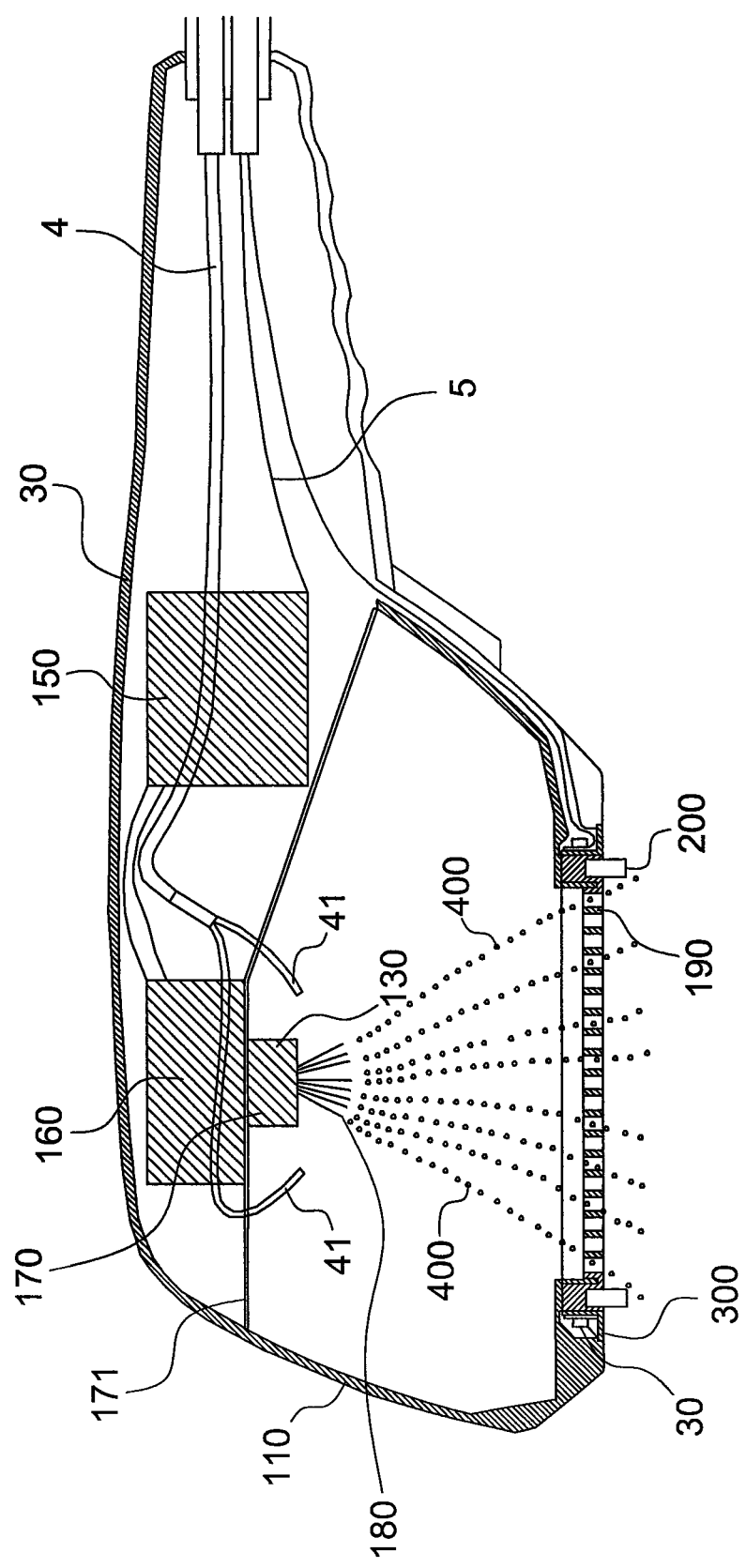
FIG. 9 is a cross-sectional view of the applicator of FIG. 6 in operation position.

Applicator 30, better shown in FIG. 7-9, includes a diffuser 110 wherein the air from the electric pump 8 is conveyed through the connecting tube 4. The diffuser 110 includes a bottom grid 190 (FIGS. 8 and 9) of a non-conductive material adapted to diffuse air or oxygen, so that these gases may affect a larger area.

Within applicator 30, a transformer 150 connected to the power stage 10 by means of the electric cable 5 is present and having the second electric signal S2 in input. Transformer 150 has the function of modifying the voltage and the current of the second electric signal S2, providing a third electric signal S3 in output with a sawtooth waveform, with a maximum voltage value of about 5 KV, with a current value of about 10 mA and which maintains the frequency value of the second electric signal S2.

To increase the value of the voltage of the third electric signal S3, downstream of transformer 150, a voltage multiplier 160 is present (FIGS. 8 and 9), which in turn comprises a plurality of diode-capacitor multiplier cells. For example, the voltage multiplier 160 comprises 8 multiplier cells.

The voltage multiplier 160 is adapted to receive the third electric signal S3 and to provide a fourth electric signal S4 in output which is rectified and is equal to the maximum value of the third electric signal S3 multiplied by the diode-capacitor multiplier cells present in the voltage multiplier 160 (in this case multiplied by 12). Typically, the voltage value of the fourth electric signal S4, which, as said, is a continuous signal, is about 6-60 KV.

The fourth electric signal S4 is provided to an electrode 170 adapted to generate the electric field to be applied on the tissue injury; electrode 170 is connected to a dividing wall 171 adapted to separate the zone of applicator 30 which contains the voltage multiplier 160 and transformer ISO from the area of the diffuser 110 which comprises electrode 170 and two tubes 41 which extend from the tube 4.

Electrode 170 is placed internally within the diffuser 110 and includes a cylindrical element 130 of a plastic material from which a plurality of threadlike conductive elements 180, preferably carbon-based, are provided, from which a plurality of electric discharges 400 are generated. Preferably, the applicator is configured to convey said electric discharges to the grid 190; in feet, the threadlike conductive elements 180 are arranged so that the generated electric field invades the whole grid 190, as shown in FIG. 9.

The grid 190 is placed in front of the threadlike conductive elements 180 at a safety distance of about 60-63 mm in such a way as to avoid the direct contact of the threadlike conductive elements 180 with the patient, but especially to apply a suitable value electric field on the tissue injury, considering that the dielectric strength of the humid air is about 1 KV/mm.

Preferably, a disposable annular spacer element 200, having a thickness of about 5 mm and preferably a depth of 12 mm and preferably a length of 420 mm, is placed on the peripheral part 130 of the grid 190 to avoid direct contact of the grid 190 with the tissue injury to externally surround the tissue injury to be treated.

Since electrode 170 is at a high electric potential (6-60 KV), the charge density tends to be greater in the free end of each threadlike conductive element 180 (for the phenomenon known as "dispersing power of the tips"), producing an electric field at the free ends which is greater than in the rest of electrode 170. By means of a regulator, it is possible to modify the electric field by varying the electric potential of electrode 170.

In addition, the high electric field of the tips causes the ionization of the air flow which is conveyed within the diffuser 110, triggering a plurality of electric discharges (the so-called "crown effect") from the free ends of each of the conductive elements 180. The modification of the electric potential applied to electrode 170 results in an increase or a decrease in the electric discharges generated by the crown effect; specifically, the electric discharges increase as the electric potential increases on electrode 170.

The presence of the return electrode 120 (FIG. 6), electrically connected through an electric cable 12 to a reference potential V1, for example 10 milliVolt, and applied to the patient via, e.g. a patch in a position near to the tissue injury, and the arrangement of applicator 30 on the tissue injury allow to convey the electric discharges generated by the conductive elements 180 on the tissue injury.

The passage of air conveyed within the diffuser 110 by the electric discharges results in the production of ozone, according to the chemical reaction $3O_2 \rightarrow 2O_3$. Therefore, the modification of the electric potential applied to electrode 170 has also the effect, of increasing or decreasing the ozone concentration (the emitted ozone concentration becomes greater as the electric potential increases over electrode 170), concentration which can also be modified by adjusting the air flow generated by the electric pump 8.

In the operation, when the apparatus 1 is used for the therapeutic treatment of a tissue injury, applicator 30 is positioned on the area to be treated so that the annular spacer element 200 is in contact with the skin of the patient or user.

When operated in the working position (FIG. 9), the electric pump 8 generates an air flow that can be controlled by a first regulator 80, to increase or decrease the ozone concentration to be produced. The air flow generated by the electric pump 8 flows through the connecting tube 4 and is collected and conveyed within the diffuser 110 by the tubes 41.

At the same time, the apparatus 1 generates, at the conductive elements 180, a high electric field which is adjustable through a second regulator, modifying the electric potential applied to electrode 170.

The return electrode 120 is placed in contact with the patient, in such a way that the electric field primarily affects the area of the tissue injury and then discharges to the return electrode. The effect of the electric field is to improve the cellular respiration and accelerate the cellular exchange, resulting in the reconstruction of the injured tissue.

The electric field also causes the ionisation of the flow of air conveyed within the diffuser 110, triggering the electric discharges that, starting from the threadlike conductive members 180 of electrode 170, discharge, through the patient, to the return electrode 120. Such electric discharges transform the air flow conveyed within the diffuser 110 into an ozone flow, with a concentration also determined by regulation through the second regulator of the potential on electrode 170. The ozone flow is diffused and directed to the tissue injury and, as said, has the effect of improving the blood ability to bring oxygen to the tissues, stimulate the reactivation of the enzymatic antioxidant defense systems of the organism, and is a potent agent against bacteria, fungi, viruses and parasites.

A LED belt 301 is provided, whose ignition indicates the good operation of the apparatus according to the invention, and a transparent cover 300 for protecting the LED belt 301.

Figure 6:
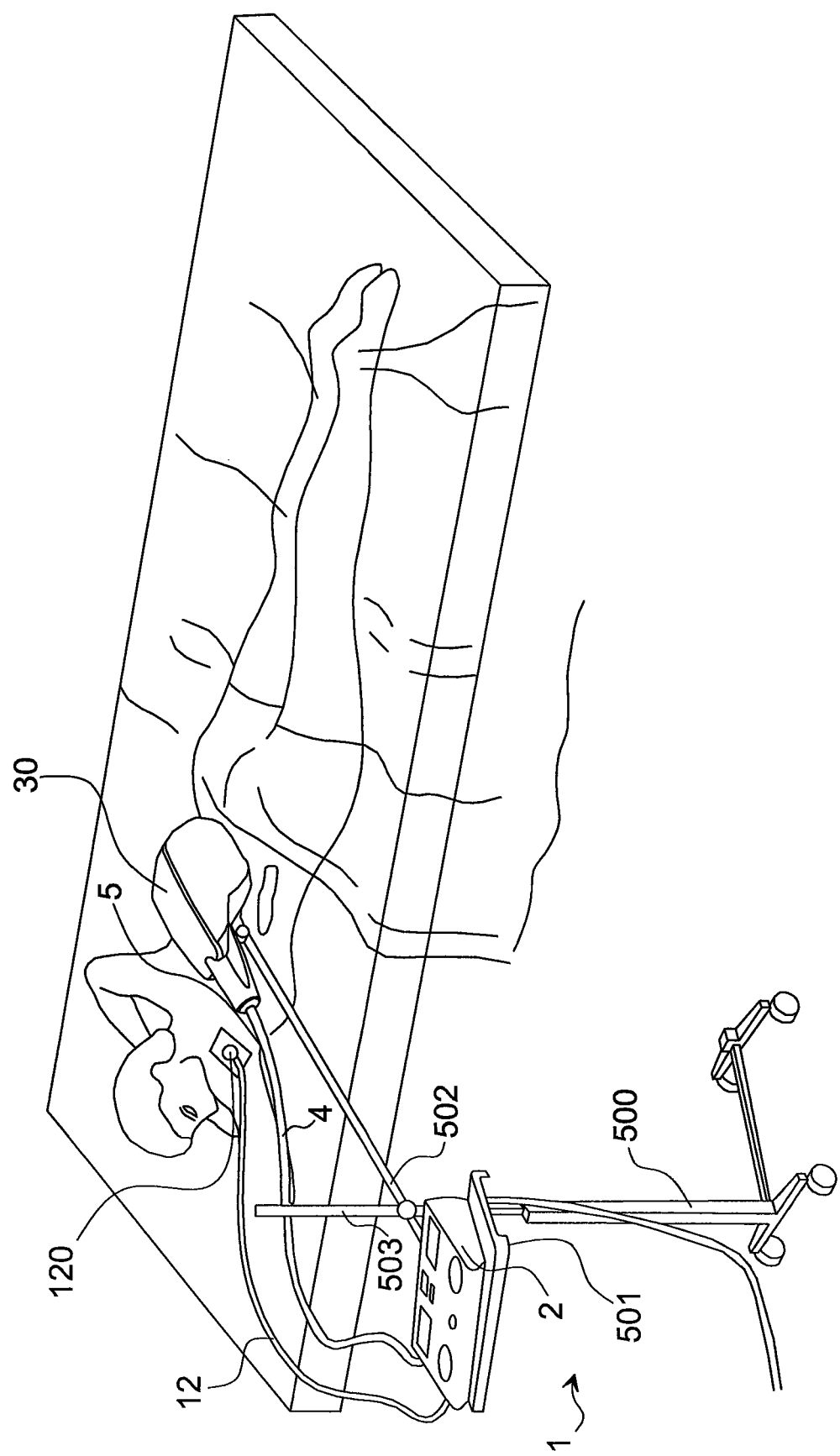
FIG. 6 shows a schematic view of ail apparatus for the therapeutic treatment of a tissue injury according to a second embodiment of the present invention.

A mobile support structure 500 is provided for the apparatus according to the invention, as can be seen in FIG. 6. The support structure 300 comprises a tray 501 for supporting the unit 2, a height adjustable, also telescopically, vertical rod 503 to which the tray 501 is connected, an arm 502, preferably telescopic, rotatably pivoted to said rod 503 in one end and rotatably pivoted to applicator 30 in the other end.

Preferably, the treatment provides for daily sessions, each of 15-30 minutes, depending on the case.

Due to the combination of electric field and ozone generated by the apparatus, according to the present invention, there is therefore a synergistic enhancement of the therapeutic effect on the tissue injury, with a healing time of the tissue injuries that can be considerably reduced with respect to the known treatment techniques.

The invention claimed is:

1. An apparatus for the therapeutic treatment of a user's tissue injury comprising a control unit to which an applicator adapted to be positioned in proximity of the tissue injury to be treated is connected, the control unit being configured to generate at the applicator an electric field adapted to be applied to the tissue injury, the apparatus it comprises a return electrode, electrically connected to a reference potential and adapted to be applied to the user in proximity of the tissue injury to be treated, the applicator is adapted to be placed on the tissue injury to concentrate the electric field on the tissue injury and the control unit is also configured to generate an air or oxygen flow which is directed to the applicator and to transform, at the applicator, the air or oxygen flow into an ozone flow adapted to be diffused and applied to the tissue injury in combined action with the electric field, the control unit comprises at least an electric pump adapted to generate the air or oxygen flow which is sent to the applicator through a connecting tube, the electric pump being provided with a first regulator by means of which to start, modify or stop the air or oxygen flow which is sent to the applicator and, consequently, the concentration of the generated ozone flow, the applicator comprises a diffuser adapted to collect the air or oxygen flow which is generated by the electric pump and arrived through the connecting tube, the diffuser comprising a bottom grid for diffusing the ozone flow obtained through the transformation of the air and oxygen flow conveyed therein, the return electrode comprises a central hole through which a screw stem is inserted in electric contact and a plurality of sharp conductive elements which extend from a conductive plate, the sharp conductive elements being adapted to trigger in their correspondence a plurality of electric discharges through the air or the oxygen conveyed within the diffuser, producing said ozone flow, the electrode is inferiorly fixed to a high voltage generator by means of a locking nut provided with a further sharp conductive element and adapted to be screwed on a screw stem.

2. The apparatus according to claim 1, wherein the control unit comprises:
an oscillator adapted to generate a first electric signal with a rectangular waveform having a given frequency,
a power stage, placed downstream of the oscillator, adapted to amplify the first electric signal and output a second electric signal again with a rectangular waveform,
and the applicator comprises:
a high voltage generator in turn comprising a transformer, connected to the power stage having the second electric signal input, the transformer being adapted to change the voltage and the current of the second electric signal, supplying at the output a third electric signal with a sawtooth waveform which maintains the frequency of the second electric signal, and a voltage multiplier comprising a plurality of diode-capacitor multiplier cells, the voltage multiplier being adapted to receive the third electric signal and to provide an output by means of a screw stem, a fourth rectified electric signal which is equal to the maximum value of the third signal multiplied by the number of multiplier cells which are present in the voltage multiplier, an electrode, to which the fourth electric signal is applied, adapted to generate the electric field and to ionize the air or oxygen flow conveyed within the diffuser for the production of the ozone flow.

3. The apparatus according to claim 1, wherein the gird comprises an annular space element adapted to contact the user's skin in proximity of the tissue injury, avoiding direct contact of the grid with the tissue injury.

4. The apparatus according to claim 1, wherein the grid comprises a plurality of pins adapted to contact the user's skin in proximity of the tissue injury, avoiding direct contact of the grid with the tissue injury.

5. The apparatus according to claim 1, wherein it has a movable support structure comprising:
a tray for the support of the control unit,
a vertical rod adjustable in height to which the tray is connected,
an adjustable arm which is rotatably pivoted to the vertical rod at an end and rotatably engage to the applicator at the other end.

6. An apparatus for the therapeutic treatment of a user's tissue injury comprising a control unit to which an applicator adapted to be positioned in proximity of the tissue injury to be treated is connected, the control unit being configured to generate at the applicator an electric field adapted to be applied to the tissue injury, the apparatus it comprises a return electrode, electrically connected to a reference potential and adapted to be applied to the user in proximity of the tissue injury to be treated, the applicator is adapted to be placed on the tissue injury to concentrate the electric field on the tissue injury and the control unit is also configured to generate an air or oxygen flow which is directed to the applicator and to transform, at the applicator, the air or oxygen flow into an ozone flow adapted to be diffused and applied to the tissue injury in combined action with the electric field, the applicator comprises an electrode electrically connected to a central unit, the electrode comprising a plurality of threadlike conductive elements, the threadlike conductive elements being adapted to trigger at their free ends a plurality of electric discharges, the applicator being configured in such a way as being adapted to convey the electric discharges to the tissue injury, the electric discharges being adapted to ionize the air flow conveyed inside a diffuser for the production of the ozone flow.

7. The apparatus according to claim 6, wherein the control unit comprises at least an electric pump adapted to generate the air or oxygen flow which is sent to the applicator through a connecting tube, the electric pump being provided with a first regulator by means of which to start, modify or stop the air or oxygen flow which is sent to the applicator and, consequently, the concentration of the generated ozone flow.

8. The apparatus according to claim 7, wherein the applicator comprises a diffuser adapted to collect the air or oxygen flow which is generated by the electric pump and arrived through the connecting tube, the diffuser comprising a bottom grid for diffusing the ozone flow obtained through the transformation of the air and oxygen flow conveyed therein.

9. The apparatus according to claim 8, wherein the return electrode comprises a central hole through which a screw stem is inserted in electric contact and a plurality of sharp conductive elements which extend from a conductive plate, the sharp conductive elements being adapted to trigger in their correspondence a plurality of electric discharges through the air or the oxygen conveyed within the diffuser, producing said ozone flow.

10. The apparatus according to claim 9, wherein the electrode is inferiorly fixed to a high voltage generator by means of a locking nut provided with a further sharp conductive element and adapted to be screwed on a screw stem.

11. The apparatus according to claim 8, wherein the grid comprises an annular spacer element adapted to contact the user's skin in proximity of the tissue injury, avoiding direct contact of the grid with the tissue injury.

12. The apparatus according to claim 8, wherein the grid comprises a plurality of pins adapted to contact the user's skin in proximity of the tissue injury, avoiding direct contact of the grid with the tissue injury.

13. The apparatus according to claim 6, wherein the control unit comprises:
an oscillator adapted to generate a first electric signal with a rectangular waveform having a given frequency,
a power stage, placed downstream of the oscillator, adapted to amplify the first electric signal and output a second electric signal again with a rectangular waveform,
and that the applicator comprises:
a transformer, connected to a power stage and having an input the second electric signal, the transformer being adapted to change the voltage and the current of the second electric signal, supplying as the output a third electric signal with a sawtooth waveform which maintains the frequency of the second electric signal, and a voltage multiplier comprising a plurality of diode-capacitor multiplier cells, the voltage multiplier being adapted to receive the third electric signal and to provide as output a fourth rectified electric signal which is equal to the maximum value of the third signal multiplied by the multiplier cells which are present in the voltage multiplier,
an electrode, to which the fourth electric signal is applied, adapted to generate the electric field and to ionize the air or oxygen flow conveyed inside a diffuser for the production of the ozone flow.

14. The apparatus according to claim 6, wherein it has a movable support structure comprising:
a tray for the support of the control unit,
a vertical rod adjustable in height to which the tray is connected, an adjustable arm which is rotatably pivoted to the vertical rod at an end and rotatably engaged to the applicator at the other end.

* * * * *